(12) United States Patent
DeBuys et al.

(10) Patent No.: US 11,712,313 B2
(45) Date of Patent: Aug. 1, 2023

(54) DUAL MANIPULATION FOR ROBOTIC CATHETER SYSTEM

(71) Applicant: Siemens Medical Solutions USA, Inc., Malvern, PA (US)

(72) Inventors: Christian DeBuys, College Station, TX (US); Young-Ho Kim, West Windsor, NJ (US); Ankur Kapoor, Plainsboro, NJ (US); Tommaso Mansi, Plainsboro, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 511 days.

(21) Appl. No.: 16/907,675

(22) Filed: Jun. 22, 2020

(65) Prior Publication Data
US 2021/0022816 A1 Jan. 28, 2021

Related U.S. Application Data (63) Continuation-in-part of application No. 16/809,067, filed on Mar. 4, 2020, now Pat. No. 11,590,319.
(60) Provisional application No. 62/935,831, filed on Nov. 15, 2019, provisional application No. 62/877,622, filed on Jul. 23, 2019.

(51) Int. Cl.
| | | |
|---|---|---|
| *A61B 34/37* | (2016.01) | |
| *B25J 9/10* | (2006.01) | |
| *A61M 25/01* | (2006.01) | |
| *A61B 34/30* | (2016.01) | |
| *A61B 90/00* | (2016.01) | |

(52) U.S. Cl.
CPC .............. *A61B 34/37* (2016.02); *A61B 90/36* (2016.02); *A61M 25/0113* (2013.01); *A61M 25/0116* (2013.01); *B25J 9/1035* (2013.01); *A61B 2034/301* (2016.02); *A61B 2090/378* (2016.02)

(58) Field of Classification Search
CPC .......... A61M 25/0113; A61M 25/0116; A61M 90/36; B25J 9/1035; A61B 2034/301; A61B 34/37; A61B 34/30; A61B 2034/302; A61B 2034/303; A61B 34/71; A61B 2090/378; A61B 2017/00464; A61B 2017/00477
See application file for complete search history.

(56) References Cited

U.S. PATENT DOCUMENTS

| | | | | |
|---|---|---|---|---|
| 5,913,857 A | * | 6/1999 | Ritchart | ............. A61B 18/1482 606/45 |
| 2011/0040150 A1 | * | 2/2011 | Govari | ................... A61B 34/30 600/117 |

(Continued)

OTHER PUBLICATIONS

German Patent Application No. DE 102019214868.9, filed on Sep. 27, 2019.

(Continued)

*Primary Examiner* — Tan-Uyen T Ho
*Assistant Examiner* — Regina Vahey (57) ABSTRACT

For robotically operating a catheter, translation and/or rotation manipulation is provided along the shaft or away from the handle, such as near a point of access to the patient. A worm drive arrangement may allow for both translation and rotation of the shaft. Some control may be provided by robotic manipulation of the handle, while other control (e.g., fine adjustments) are made by robotic manipulation of the shaft.

19 Claims, 4 Drawing Sheets

(56) References Cited

U.S. PATENT DOCUMENTS

| | | | |
|---|---|---|---|
| 2015/0073339 A1* | 3/2015 | Pacheco | A61M 25/0113 604/95.01 |
| 2017/0065396 A1* | 3/2017 | Look | A61B 17/22 |
| 2017/0095299 A1* | 4/2017 | Hendrick | A61B 34/30 |
| 2017/0304015 A1* | 10/2017 | Tavallaei | A61B 34/20 |
| 2020/0060646 A1 | 2/2020 | Lindenroth | |
| 2020/0061339 A1 | 2/2020 | Lindenroth | |

OTHER PUBLICATIONS

Stereotaxis, "Stereotaxs V-Drive Robotic Navigation System," Stereotaxis, [Online]. Available: http://www.stereotaxis.com/products/#!/vdrive. Accessed: Feb. 19, 2020.

Loschak, Paul M., et al. "A 4-DOF robot for positioning ultrasound imaging catheters." ASME 2015 International Design Engineering Technical Conferences and Computers and Information in Engineering Conference. American Society of Mechanical Engineers Digital Collection, 2015.

* cited by examiner

DUAL MANIPULATION FOR ROBOTIC CATHETER SYSTEM

RELATED APPLICATION

The present patent document is a continuation-in-part of U.S. patent application Ser. No. 16/809,067, filed Mar. 4, 2020, which claims the benefit of the filing date under 35 U.S.C. § 119(e) of Provisional U.S. Patent Application Ser. No. 62/877,622, filed Jul. 23, 2019, and claims the benefit of the filing date under 35 U.S.C. § 119(e) of Provisional U.S. Patent Application Ser. No. 62/935,831, filed Nov. 15, 2019, which are all hereby incorporated by reference.

BACKGROUND

The present embodiments relate to robotic control of a medical catheter. One example medical catheter is an intra-cardiac echocardiography (ICE) catheter, which is used for cardiac interventional and diagnostic procedures. ICE is able to provide close feedback of anatomical structures and tools during a surgical procedure.

One major challenge ICE and other interventional catheterization poses for the operating interventionalist is the difficult catheter manipulability. The ICE catheter is moved in a coordinated fashion with an interventional catheter. The operator manipulates multiple degrees of freedom simultaneously to achieve a desired pose as well as manages the coordination. A robotic system that controls the degrees of freedom (DOFs) of an ICE catheter may reduce the cognitive strain on the user.

A commercially-available robotic system for ultrasound catheter manipulation is the STEREOTAXIS VDRIVE system. The mechanical design of this system controls only a limited number of degrees of freedom of the ICE catheter. For example, the precise control of the orientation of the catheter, which is necessary for appropriate imaging, may not be provided. Additionally, all motions are done at the handle, failing to account for the possibility of catheter buckling. Another proposed, automated system for a hand-held ICE catheter has a large footprint and may be difficult to sterilize, making it unusable in a clinical setting.

SUMMARY

By way of introduction, the preferred embodiments described below include methods, systems, and robots for robotically operating a catheter. Translation and/or rotation manipulation is provided along the shaft or away from the handle, such as near a point of access to the patient. A worm drive arrangement may allow for both translation and rotation of the shaft. Some control may be provided by robotic manipulation of the handle, while other control (e.g., fine adjustments) are made by robotic manipulation of the shaft.

In a first aspect, a robotic catheter system includes a threaded housing configured to hold a shaft of a catheter at a position spaced from a handle of the catheter. A first gear mates with the threaded housing. The first gear and the threaded housing form a worm drive. A motor is configured to rotate the first gear. The threaded housing is movable in response to rotation of the gear such that the shaft of the catheter is moved.

For translation, the threaded housing is a worm with threading on an outer surface of a cylinder. The first gear is a tube with threading on an inner surface and gearing on an outer surface (e.g., face gear with internal gearing). The threading on the inner surface mates with the threading on the outer surface. For rotation, the threaded worm has a groove extending along an outer surface of the cylinder. The first gear is a first tube with a tooth on an inner surface. The tooth mates with the groove. For both translation and rotation, the first gear is arranged for one of translation or rotation. A second gear is arranged for the other of translation or rotation.

The worm drive, in response to operation of the motor, is configured to rotate the shaft about a longitudinal axis of the shaft. The worm drive, in response to operation of the motor, is configured to translation the shaft along a longitudinal axis of the shaft. For both translation and rotation, a transmission or separate motors are used to operate the worm drive.

The motor is a servo motor in one embodiment. Other types of motors, such as step motors or actuators, may be used. For operation of the first gear, the first gear has teeth on an outer surface. The motor rotates the first gear by rotating a shaft with gearing mating with the teeth.

In one embodiment, the robotic catheter system also includes a housing housing the motor, a base connectable with the handle of the catheter and configured for robotic manipulation of the handle, and an armature connecting the housing to the base. In a further embodiment, the armature is configured to hold the shaft of the catheter at a point of entry into a patient. The manipulation of the handle includes rotation of the handle and/or steering of the catheter with steering wires.

In another embodiment, a housing houses the motor. A clam shell has a hinge. The clam shell is configured to accept the first gear and the threaded housing and hold the first gear and the threaded housing in place with the first gear mating with gearing connected with the motor.

In a second aspect, a method is provided for robotically operating a catheter. A robot is connected to a shaft of a catheter spaced from a handle of the catheter. The robot, at a location of the connection, translates the catheter along a longitudinal axis of the shaft. The robot, at the location of the connection, rotates the shaft about the longitudinal axis.

In one embodiment, the translation includes operating a worm drive. A worm of the worm drive connects the robot to the shaft, and a worm wheel of the worm drive connects to a motor. For example, to translate, the worm is driven along the longitudinal axis with a threaded connection to the worm wheel.

In another embodiment, the rotation includes operating a worm drive. A worm of the worm drive connects the robot to the shaft, and a worm wheel of the worm drive connected to a motor. For example, to rotate, the worm is rotated by the worm wheel. A tooth of the worm wheel is positioned in a groove on the worm.

In an embodiment, the catheter is operated at the handle by the robot. The translating and rotating are additional operations of the catheter at the location.

In a third aspect, a system is provided for robotic manipulation of a catheter. A handle robot is configured to hold a handle of the catheter. The handle robot has one or more first gears to operate controls of the handle of the catheter. An access point robot is configured to hold a shaft of the catheter away from the handle. The access point robot is configured to translate the shaft along a longitudinal axis of the catheter and to rotate the shaft about the longitudinal axis. A controller is configured to control operation of the first gears, the translation, and the rotation.

In one embodiment, the access point robot has a worm drive having a worm with threading and a notch. A first worm wheel has threading for the translation, and a second worm wheel has a tooth matable with the notch for the rotation.

The present invention is defined by the following claims, and nothing in this section should be taken as a limitation on those claims. Features of one aspect or type of claim (e.g., method or system) may be used in other aspects or types of claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

A compact, sterilizable robotic catheter manipulator is provided for general-purpose access points. In one embodiment, two sets of motion transmission setups are provided. The first, placed at the catheter handle as the base of the device, provides rotation of the handle, and control of the knobs that cause articulation of the flexible catheter body. The second, a front mechanism, is placed around the flexible catheter body itself and is placed near the insertion point in the patient. This second setup provides translation and rotation of the catheter while limiting buckling caused by friction from the insertion sheath. The end-effector of the medical device can be precisely positioned because the first setup can be used for larger vertical, yaw, and for-aft adjustments while the second setup may move for finer translational and angular adjustments.

The robotic system fits a standard, commercially-available ICE catheter, such as those in the ACUNAV family of catheters from Siemens. The sterile, modular robotic system provides for full-DOF robotic control of an ICE catheter. This system may be used for any kind of catheter or flexible medical instrument for insertion into a patient, including but not limited to bronchoscopes, flexible endoscopes, transthoracic echocardiography probes, trans-esophageal echocardiography probes, cardiac catheters for intervention (i.e., with medical tool for interaction with tissue of the patient), and any other type of catheter. This system may be used with a more-integrated system, in which the motion-driving elements and the imaging device are all integrated into one compact setup at production, as opposed to the embodiment described here, in which the imaging instrument and the robotic system are brought together at the time of use. Different methods for gripping and holding the catheter, for setting up the whole system, and/or for providing motion transmission may be used.

The base of the device, which includes the motors, motor drivers, and adjustable degrees of freedom for control of the handle, is general purpose in that any device that can be fitted with an appropriate transmission system may be used with the base. The adjustable degrees of freedom and compactness of the base allow for surgeries at different access points (e.g., femoral, radial, or jugular) and precise alignment of the medical instrument, such as alignment of an ICE catheter with a sheath. The base is easily attached to the operating table or to another mobile table. The posability of the modular base allows for precise alignment of the catheter with the sheath. A plastic interface between the base and a transmission holding the catheter handle allows for the base to remain sterile so that the entire base is reusable and does not need to be cleaned.

The front mechanism or robot is used in dual manipulation to mimic the finer motions that a human operator would execute with the hand that is closest to the introducer. The front mechanism may rotate and/or translate the catheter shaft close to the introducer, and the front mechanism may be used to angle the catheter so that the shaft is aligned with the introducer. The front mechanism allows the catheter shaft to be clipped onto or in the robot after the catheter has already been introduced into the human.

General purpose, dual manipulation (e.g., motion from two gripping points) provides for coupled manipulation. Fine, linear motion is provided by the robotic front mechanism connecting and operating near the insertion point of the shaft. High force and/or torque may be provided by using separate actuators for the translation and rotation. The fine motion is provided by linking the shaft of the catheter to the actuator through a worm gear with separate rotation and translation gear designs.

Figure 1:
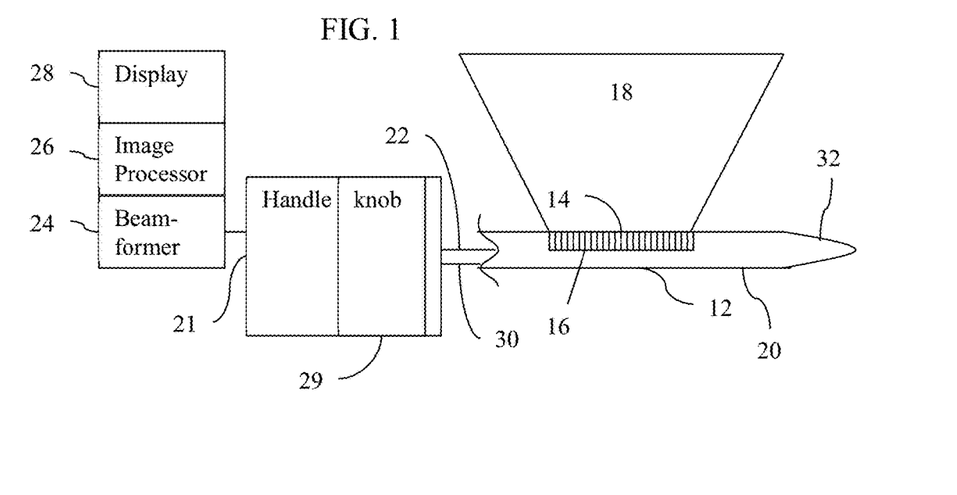
FIG. 1 is a block diagram of one embodiment of a medical ultrasound system for imaging with an ICE catheter.

FIG. 1 shows an example medical ultrasound system for ICE. This example medical ultrasound system uses the ICE catheter 12, which may be robotically controlled. The medical ultrasound system includes the ICE catheter 12, a beamformer 24, an image processor 26, and a display 28. Additional, different, or fewer components may be provided, such as providing just the catheter 12. The catheter 12 releasably connects with the imaging system.

The ICE catheter 12 includes an array 14 of elements 16 for imaging within a shaft or housing 20 having a tip 32, electrical conductors 22, steering wires 30, and a handle 21. Additional, different, or fewer components may be provided, such as radio opaque markers, ablation electrodes, lens, needle guide, or ports. In other embodiments, the catheter 12 is an ablation catheter or interventional catheter rather than an imaging catheter.

The shaft housing 20 is PEBAX, nylon, polymer, or other flexible material. The shaft housing 20 is formed around the array 14 and other parts extending from the handle 21 and insertable into the patient. The shaft housing 20 is configured for insertion into a circulatory system of a patient. For example, the distal tip 32 of the catheter 12 includes a more flexible portion covered by the shaft housing 20 for moving through the circulatory system. Steering wires 30 connected to the shaft housing 20 or parts (e.g., anchors) within the housing 20 are configured to guide the shaft housing 20 within the circulatory system.

The array 14 is positioned within the catheter 12. The array 14 may fit within 10 French, 3.33 mm, 12.5 French, or another diameter catheter 12. The array 14 is at a distal end or tip 32 of the catheter 12, such as being within 20 mm of an end of the tip 32 or a beginning of a flexible tip portion. The array 14 may have any position within the catheter 12 that results in the array 14 being within the patient during use of the catheter 12 for imaging.

The transducer array 14 is used for ultrasound imaging. The images assist in diagnosis, catheter guidance, needle guidance, ablation guidance, placement, and/or needle puncture. The array 14 scans in a field of view 18 in a plane perpendicular to the emitting face. The patient within the field of view 18 may be imaged using the array 14.

Electrical conductors 22 connect the elements 16 of the array 14 to the beamformer 24. The conductors 22 are cables, coaxial cables, traces on flexible circuit material, wires, wire jumpers, combinations thereof, and/or other now known or later developed conductor.

The beamformer 24 includes a plurality of channels for generating transmit waveforms and/or receiving signals. Relative delays and/or apodization focus the transmit waveforms or received signals for forming beams and setting a focal location. The beamformer 24 connects with the conductors 22 for applying waveforms for imaging with the array 14 and receiving signals. For imaging, the beamformer 24 selects an aperture including one, some, or all of the elements 16 of the array 14. For scanning, the beamformer 24 electronically focuses along the azimuth direction. A plurality of scan lines using an aperture is scanned. During receive operations, the focus may vary as a function of depth (i.e., dynamic focusing).

The image processor 26 is a detector, filter, processor, application specific integrated circuit, field programmable gate array, digital signal processor, control processor, scan converter, three-dimensional image processor, graphics processing unit, analog circuit, digital circuit, or combinations thereof. The image processor 26 receives beamformed data and generates images on the display 28, which is a display screen.

The steering wires 30 of the catheter 12 are used to position the array 14 (and/or medical instrument) relative to the patient. The steering wires 30 are cables, tendons, or other structure for transferring push and pull force from the handle 21 to a portion of the catheter 12 within a patient, such as to the distal end or the tip 32. Any material may be used, such as plastic, fiberglass, or metal. Any number of steering wires 30 may be used, such as three or four wires. For example, three or four steering wires 30 offset from the center in an equal spacing about the center or longitudinal axis may be used to steer along two perpendicular planes. The steering wires 30 run through the elastic material of the catheter body or shaft housing 20 to the distal end and are arranged in a circular fashion around a central channel, which provides sufficient space for the ultrasound transducer cable or conductors 22 to be guided through. The relative force between the steering wires 30 causes the catheter 12 to bend. Any now known or later developed arrangement of steering wires 30 may be used.

In one embodiment, one knob 29 is provided for controlling the bend of the distal end in one plane. Two steering wires 30 connect with the knob 29, so rotation of the knob 29 causes a change in relative pressure or force on the steering wires 30. In another embodiment, two knobs 29 are provided. One knob 29 (e.g., AP knob) is for bending in one plane, such as an anterior-posterior (AP) plane, and another knob 29 (e.g., RL knob) is for bending in a perpendicular plane, such as a right-left (RL) plane.

The knob 29 rotates to steer. The knob 29 rotates about a longitudinal axis of the handle 21 and/or catheter 12. For example, the knob 29 is a cylinder or ring on the outer housing of the handle 21 for rotation about the axis in either direction to steer. In other examples, the knob 29 rotates around an axis perpendicular to the longitudinal axis of the handle 21. Alternatively, a slider or lever is provided as the knob 29 for steering.

The steering wires 30 control the bend at a distal end of the catheter 12. The bend may be at a portion of the catheter 12 adjacent to the distal end or tip 20, such as providing for the array 14 to be spaced from the handle 21 by the bend. For example, the steering wires 30 are anchored to the shaft housing 20, transducer array 14, or a rigid insert or anchor near the distal end to cause the bend. The elastic body or shaft housing 20 may be bent along its principal axes by applying tension to the attached steering wires 30. Using motors instead of user-based rotation of two knobs for two planes allows for only three steering wires 30 for forming the bend. Four steering wires 30 with motor-based control may be used, such as where the handle 21 is designed for manual operation.

The handle 21 includes a housing and user input in the form of one or more knobs 29. The handle 21 is shaped and sized for handheld guidance or use of the catheter 12. For example, the handle 21 is cylindrical with grips to be used by one hand of a surgeon. The handle 21 has a single housing made of one or more parts. The housing connects with the shaft housing 20 of the catheter 12 and with a cable or cables for power and communications. In alternative embodiments, the housing is shaped for use with a robotic system rather than handheld guidance.

For robotic guidance, the catheter handle 21 is placed in an external actuation stage. The actuation stage is a base or handle robot formed from a motor housing. Rather than handheld use, the actuation stage provides control for rotation, steering, and/or translation via the handle 21 to be automated. The operator is then able to tele-operate the catheter 12 from a remote console, or a high-level motion planning algorithm may be used to generate spatial trajectories for the catheter tip 32.

Figure 2:
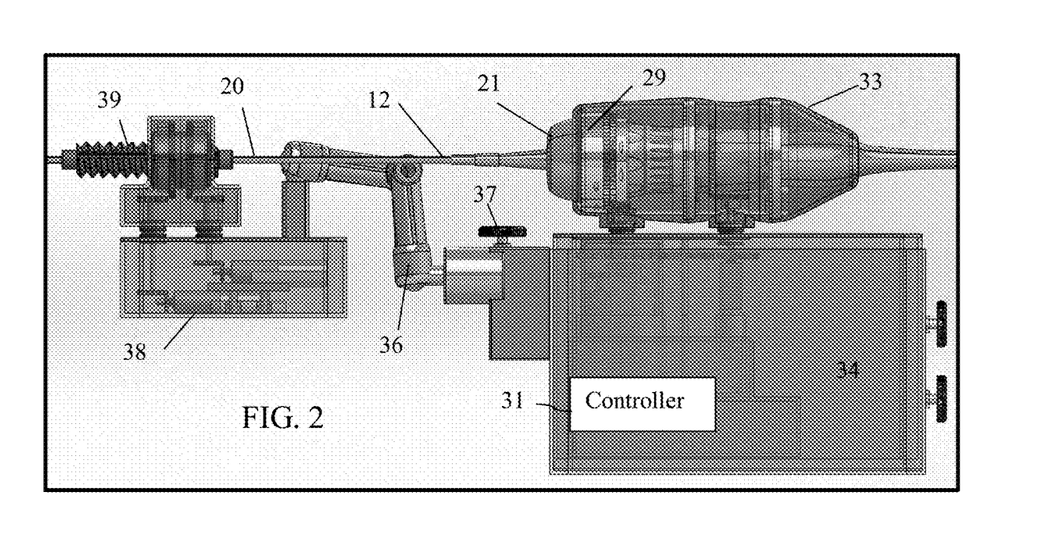
FIG. 2 illustrates one embodiment of a robotic system for guiding a catheter.

FIG. 2 shows a system for robotic manipulation of the catheter 12. The system is a robotic catheter system for rotating and/or steering the catheter 12. The system includes a base 34, a catheter handle housing 33 (carriage), an access point base 38, an access point guide 39, and an arm 36. The base 34 and catheter handle housing 33 form a handle robot. The access point base 38 and the access point guide 39 from an access point robot or front mechanism. The arm 36 connects or links the handle robot to the access point robot. Additional, different, or fewer components may be provided. For example, the arm 36 is not provided. As another example, the base 34 and the catheter handle housing 33 are combined into one housing or device. In yet another example, the access point robot is provided without the handle robot.

Each of the parts has a housing. The housings are plastic, metal, resin, silicone, or other material. The shafts and gearing are plastic, metal, or another material.

The handle robot is configured to hold a handle 21 of the catheter 12. The handle robot has one or more gears to operate controls of the handle 21 of the catheter 12. The handle robot is formed from the base 34 and the catheter handle housing 33. The handle robot is configured for robotic manipulation of the handle 21, such as rotation of the handle 21 and/or steering of the catheter 12 with the steering wires 30 through rotation of the knobs 29.

The catheter handle housing 33 is configured to hold the handle 21 of the catheter 12. Any part of the handle 21 may be held, such as surrounding 50-90% of the outer surface of the handle 21. In one embodiment, the catheter handle housing 33 is a clamshell shape with two halves. A hinge may be provided. Alternatively, the handle 21 is placed in a lower half, and then the upper half is placed over the lower half and latched to the lower half. Other arrangements, such as having two or more rings to hold the handle 21, may be used.

The electrical cables with or without an end of the handle 21 may extend out of the catheter handle housing 33 when the handle 21 is positioned in the catheter handle housing 33. The shaft housing 20 with or without another end of the handle 21 may extend out of the catheter handle housing 33 when the handle 21 is positioned in the catheter handle housing 33. The knob 29 or knobs 29 are within or at least partly within the catheter handle housing 33.

Once positioned, one or more parts, such as rubberized or coated parts, form a pressure fit with the handle 21. For example, studs or one or more rings contact the handle 21 and are movable (e.g., rotatable) within the catheter handle housing 33. A separate set of studs or a ring contacts each knob 29 and are independently moveable (e.g., rotatable) within the catheter handle housing 33. Gears may connect with each of the rotatable parts. For the handle 21, a circular gear surrounds and directly or indirectly contacts the handle 21. For the knobs 29, circular gears surround and directly or indirectly contacting the knobs 29. For example, the gears are bevel gears, but flat or straight gears or gears with tracks on the side of a disc shape (face gears) may be used. The gears in the catheter handle housing 33 provide for driven rotation of the handle 21 and/or the knobs 29.

Sets of gearing in the catheter handle housing 33 transmit force from the base 34 to the handle 21 and knobs 29. This gearing is used to control the catheter robotically, such as the gearing being for operating the anterior-posterior and/or left-right knobs 29 for steering a distal end of the catheter 12. To steer, the knobs 29 are rotated relative to the handle 21, such as about the longitudinal axis of the handle 21, by the gearing.

The base 34 includes the housing around one or more motors. The motors are within the base 34. The motors include shafts for driving the gearing in the catheter handle housing 33, allowing for robotic manipulation of the catheter handle 21 and knobs 29.

Figure 8:
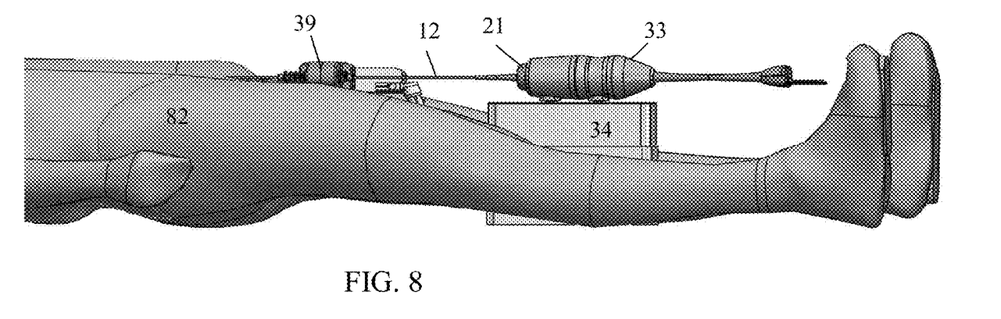
FIG. 8 illustrates positioning of a base and access point housing for robotically guiding a cardiac catheter, such as an ICE catheter.

The housing of the base 34 has any size and shape. In one embodiment, the housing is prismoid, such as having six sides. The size and shape allow for placement on or by a table on which the patient lies. For example, the housing of the base 34 is less than 16 inches long, 12 inches high, and 6 inches wide. FIG. 8 shows an example with the base 34 sized and shaped to be placed on a table between their legs of the patient 82. This modular base 34 allows for placement at any desired position and orientation. The adjustable degrees of freedom and compactness of the base 34 allow for surgeries at different access points (e.g., femoral, radial, or jugular) and precise alignment of the catheter 12 with the sheath (introducer or trocar) at the access point in the patient 82. The base 34 may be attached to the operating table or another table by magnets at the bottom (either a permanent magnet switch or electromagnets). Gravity, suction cups, latches, and/or other attachment devices may be used. Larger height, width, and/or length may be used.

The base 34 connects with the catheter handle housing 33. A plastic, metal, or other transmission may be used to transfer force from the motors to the gearing. The rotations, including speed, direction, and amount, of the handle 21 and knobs 29 are driven from the base 34.

In one embodiment, the base 34 connects to the gearing through a plastic interface of a sterile bag. The sterile bag includes one or more holes for the shafts connecting the motors to the gearing. The catheter handle housing 33 and access point housing 39 are outside of the sterile bag while the base 34, arm 36, and access point base 38 are in the sterile bag, allowing re-use with less cleaning and avoiding discarding of expensive parts. Since all electronics in the base 34 are kept sterile in a procedure, the base 34 and electronics may be reused without cleaning. Since all parts not inside the bag are plastic or metal (i.e., the catheter handle housing 33, gearing inside the catheter handle housing 33, access point guide 39, and worm gear inside the access point guide 39), these parts may be easily cleaned and reused.

The arm 36 extends from the base 34. The arm 36 includes any number and/or type of joints. For example, four links with three elbow joints are used. The arm 36 latches to or is formed as part of the base 34. Other connections to the base 34 may be used. Alternatively, the arm 36 mounts to the table or other device and is not connected directly to the base 34. The arm 36 is metal, rubber, fiberglass, plastic, and/or resin. The arm 36 may change position by manual adjustment. Alternatively, servo motors under electrical control adjust one or more joints. Any number of degrees of freedom may be provided.

The arm 36 supports the access point housing 39 and the access point base 38. The access point base 38 may include motors and gearing for moving an orientation (rotation) and/or position (translation) of the access point housing 39. The access point housing 39 holds the catheter 12, such as the shaft housing 20, at the access point or entry point into the patient. For example, the shaft housing 20 extends through an aperture formed by the access point housing 39, which is elongated to assist in preventing buckling.

The arm 36 provides an initial positioning and orientation of the access point housing 39 away from the handle 21 of the catheter 12 and away from the base 34. The position and/or orientation of the access point housing 39 may be further adjusted in three dimensions using the poseable arm 36 in order to achieve the desired end-effector angle. The access point base 38 may manipulate the flexible catheter 12 itself, providing more direct control of the flexible catheter body or shaft housing 20 near its insertion point. This control or manipulation of the position and angle by the access point may reduce the chance of the catheter 12 buckling when pushed, pulled, or rotated in relation to the insertion sheath.

The access point robot (e.g., access point housing 39 and access point base 38) is configured to hold the shaft 20 of the catheter 12 away from the handle 21. For example, the shaft 20 is contacted 3-18 inches from the handle 21 and within 1-8 inches of an introducer or trocar. The access point robot is configured to translate the shaft 20 along a longitudinal axis of the catheter 12 and/or to rotate the shaft 20 about the longitudinal axis. Other motions may be provided, such as bending the shaft 20.

Figure 3:
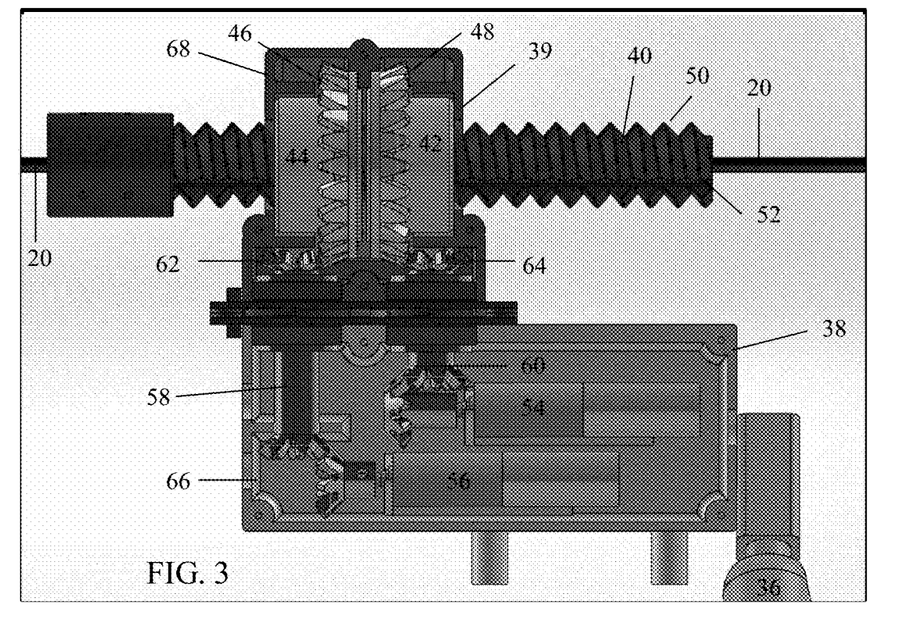
FIG. 3 illustrates one embodiment of a shaft manipulation robot for guiding a catheter.

FIG. 3 shows a side view without intervening coverings of one embodiment of the access point robot. A worm gear or drive formed by a worm 40 and one or more worm gears 42, 44 is held in place by a housing 68 as the access point housing 39. The worm gear 42 provides for translation of the shaft 20 by the worm drive, and/or the worm gear 44 provides for rotation of the shaft 20 by the worm drive. The housing 68 releasably mounts to the access point base 38. Additional, different, or fewer components may be provided. For example, the base 39 and housing 68 are integrated as one device.

The worm 40 is a metal, plastic or other material cylinder. The interior of the cylinder is shaped and sized to provide a press or friction fit with the shaft 20. The shaft 20 may be slid through the worm 40 by application of force. Friction or pressure holds the shaft 20 within the worm 40 in a way allowing the hold to be overcome or in a way to prevent slipping. Alternatively, the worm 40 is a clamshell, and the shaft 20 is placed inside a half of the worm 40, and the rest of the worm 40 is clamped or held down on the shaft 20. Other arrangements may be used, such as an iris that closes around the shaft 20 to hold the shaft 20 within the worm 40. Any gripping arrangement may be used to grip the shaft 20 once inserted into the worm 40. The worm 40 holds the shaft 20 at the position spaced from the handle 21, such as holding over a 2-8 inch length of the shaft 20.

The worm 40 includes threading 50 (screw thread) on an outer surface. The threading 50 has any desired lead, pitch, and start. The threading 50 is provided for interaction with the translation gear 42 for translating the shaft 20 longitudinally (i.e., applying translation force along a longitudinal axis of the shaft 20).

Alternatively or additionally, the worm 40 includes one or more (e.g., three) notches 52. The notch 52 is a groove or hole at a different angle than the threading 50. The notch 52 is on the outer surface of the worm 40. In FIG. 3, the notch 52 extends along an entire or substantial (e.g., 75% or more) length of the worm 40. In other embodiments, the notch 52 is a hole or indentation with any length, such as a length slightly greater than a length of a tooth or extension 70 on the rotation worm gear 44.

A rotation gear 44 and a translation gear 42 mate with the worm 40. The rotation gear 44 and the translation gear 42 are face gears with internal gears for mating with the worm 40. Other types of gearing may be used, such as spur, helical, bevel, or screw gears. This mated structure forms the worm drive or gearing. In other embodiments, only the translation gear 42 (i.e., without the rotation gear 44) or vice versa are provided. In yet other embodiments, additional worm gears are provided.

Figure 4:
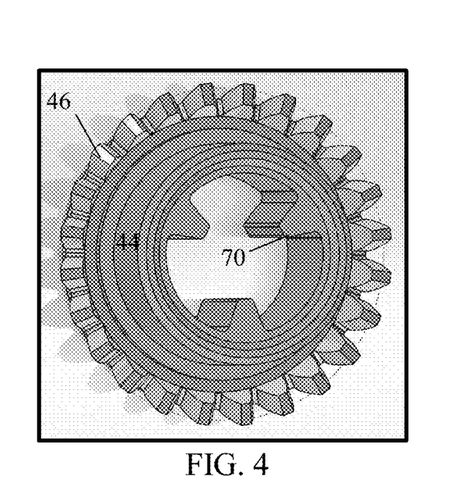
FIG. 4 shows a gear for rotation in a worm drive of the robot of FIG. 3, according to one embodiment.

FIG. 4 shows one example of the rotation gear 44. The rotation gear 44 is metal, plastic, or another material. The rotation gear 44 is a tube, such as having a generally washer or another cylindrical shape. An outer surface and an inner surface are provided.

An outer edge or the outer surface includes the gearing or teeth 46. The gearing or teeth 46 are at any angle relative to a plane orthogonal to a center axis (i.e., longitudinal axis of the shaft 20 in the arrangement shown in FIG. 3).

The inner surface includes one or more teeth 70. The tooth or teeth 70 are sized and shaped to fit in or mate with the notch 52. In the example of FIG. 4, the three teeth 70 are provided as ridges that fit within the notch 52 when the gear 44 is placed over the worm 40. The teeth 70 may slide longitudinally within the notch 52 but prevent rotation of the notch 52 or worm 40 without rotation of the rotation gear 44. The tooth 70 mating with the groove 52 allows translation while the rotation gear 44 is not rotated and causes rotation of the worm 40 while the rotation gear 44 is rotated. The inner teeth 70 grip the worm 40 for rotating but allow translation. The rotation gear 44 and translation gear 42 are rotated together (same direction and magnitude) to achieve just rotation of the shaft 20 of the catheter 12. The translation gear 42 may be rotated while keeping the rotation gear 44 fixed to achieve just translation. The rotation gear 44 may slide along the worm 40 in translation without rotating.

Other rotation gear 44 designs may be used. The rotation gear 44 includes gearing or other mechanism to receive movement from a motor, and gearing 46 or other mechanism to transfer the movement as rotation to the worm 40.

Figure 5:
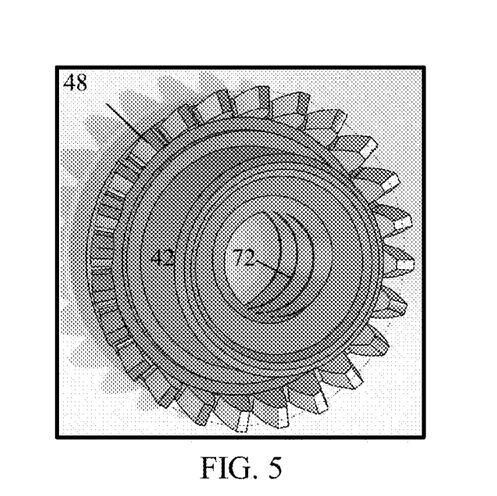
FIG. 5 shows a gear for translation in a worm drive of the robot of FIG. 3, according to one embodiment.

FIG. 5 shows one example of the translation gear 42. The translation gear 42 is metal, plastic, or another material. The translation gear 42 is a tube, such as having a generally washer or another cylindrical shape. An outer surface and an inner surface are provided.

An outer edge or the outer surface includes the gearing or teeth 48. The gearing or teeth 48 are at any angle relative to a plane orthogonal to a center axis (i.e., longitudinal axis of the shaft 20 in the arrangement shown in FIG. 3).

The inner surface includes threading 72. The threading 72 is sized and shaped to fit in or mate with the threading 50 of the worm 40. The translation gear 42 has a screw profile matching the worm 40. The threading 72 mating with the threading 50 provides for translation of the worm 40 relative to the translation gear 42. Rotation of the translation gear 42 causes the worm 40 to translate the shaft 20 along the longitudinal axis. By holding the rotation gear 44 in place (i.e., preventing rotation), the rotation of the translation gear 42 causes the worm 40 to translate without rotation due to the threads 50, 72. The translation gear 42 may be rotated while keeping the rotation gear 44 fixed to achieve just translation. The rotation gear 44 may slide along the worm 40 in translation without rotating. Translation and rotation may be provided at the same time by operating the rotation and translation gears 44, 42 at different speeds of rotation.

Referring again to FIG. 3, the rotation and translation gears 44, 42 connect to motors 54, 56, respectively. The motors 54, 56 are in the access point base 38, such as within the metal or plastic housing 66. The motor shafts connect through gearing, such as bevel gears, to shafts 58, 60. The shafts 58, 60 includes bevel gears 62, 64, which mate with the gearing 46, 48. Rotation by the motor 54 causes the shaft 60 to rotate, which rotates the translation gear 42. Rotation by the motor 56 causes the shaft 58 to rotate, which rotates the rotation gear 44. The mating of the various gearings provides a transmission of force from the motors 54, 56 to the rotation and translation gears 44, 42.

The motors 54 and 56 are servo motors, rotational motors, linear motors (e.g., linear magnetic motors), or other electric, pneumatic, or hydraulic motors for rotating the shafts 58 and 60. Alternatively, gearing, clutch, and/or transmission is used to apply force from one motor to multiple shafts 58, 60. In order to keep the electronics sterile, the motors 54 and 56 are spaced away from the catheter 12 by being positioned in the base 38.

In response to operation of the motor 56, the worm drive is configured to rotate the shaft 20 about a longitudinal axis of the shaft 20. This twists the shaft, providing fine rotation motion along the shaft 20 for use of the catheter 12 in imaging or other purpose. The motor 54 operates to rotate the translation gear 42 at a same rate as the rotation gear 44 to prevent translation while rotating the shaft 20. In response to operation of the motor 54, the worm drive is configured to translate the shaft 20 along the longitudinal axis of the shaft 20. This stretches the shaft 20 or pulls the shaft further into or out of the patient. The motor 56 is not operated and/or braked so that the worm 40 does not rotate, transferring the rotation of the translation gear 42 to translation of the worm 40.

The housing 66 is metal, plastic, or another material. The housing 66 encloses the motors 54, 56 and part of the shafts 58, 60. The shafts 58, 60 extend from the housing 66, such as through a sterile barrier with holes for the shafts 58, 60. The shafts 58, 60 mate with the rotation and translation gears 44, 42 in another housing 68.

The housing 68 is a plastic, metal, or other material. The housing 68 holds the worm drive relative to the shafts 58, 60. As shown in FIG. 3, the housing 68 provides for rotation of the gears 42, 44 while holding the gearing 46, 48 against the gears 62, 64.

Figure 6A:
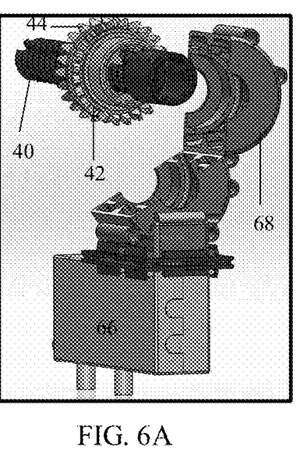
FIGS. 6A-C shows one embodiment of a clamshell arrangement for use of the robot of FIG. 3 with a catheter.
Figure 6B:
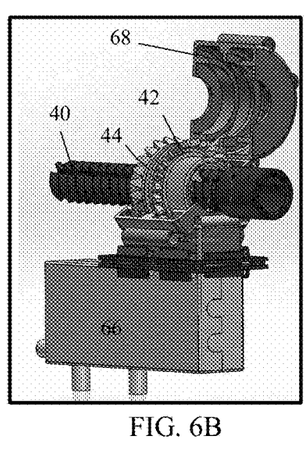
Figure 6C:
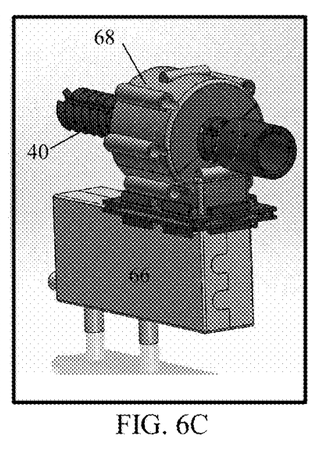

In one embodiment, the housing 68 is a clamshell with a hinge. FIGS. 6A-C show an example. The clamshell is configured to accept the worm drive (i.e., the worm 40 or another threaded housing of the shaft 20 and the rotation and/or translation gears 44, 42). The worm drive may be connected with the catheter 12. For example, the shaft 20 is slid through the worm 40 and into the patient. The worm 40 may be slid along the shaft 20 towards or against the base 34 during introduction of the shaft 20 into the patient. Once the shaft 20 is positioned in the patient, the worm 40 may be slid back to the access point, such as slid to the access point base 38 and clamshell (i.e., housing 68). The worm 40 may then grip the shaft 20, such as closing an iris or tightening a fit.

Once positioned for imaging or other use, the worm drive is positioned adjacent to the clamshell as shown in FIG. 6A. The worm drive is then placed into the clamshell as shown in FIG. 6B. The translation and rotation gears 44, 42 are placed into the clamshell and mated with the gears 62, 64. The clamshell is then closed over the worm drive to hold the worm drive in place as shown in FIG. 6C for operation of the access point robot. The use of the clamshell may keep the access point base 38 and the clamshell out of the way during introduction of the catheter 12 into the patient. In other embodiments, the worm 40 has a clamshell or opening design so the worm 40 is not positioned onto the shaft 20 until after introduction into the patient 82.

Referring again to FIG. 2, the controller 31 controls the robotic guidance. The same or different controllers 31 control the handle robot and the access point robot. The manipulation by the access point robot (e.g., translation and/or rotation of the shaft) may be independent of the manipulation by the handle robot. In other embodiments, the handle robot is controlled in conjunction with the access point robot, such as both translating and/or rotating the shaft.

The controller 31 is a processor, application specific integrated circuit, integrated circuit, digital signal processor, field programmable gate array, or other control device for controlling the motors of the robotic system. The controller 31 is configured by design, hardware, and/or software to translate and/or rotate the shaft 20 using control from a user interface or input or other controls. The controller 31 is configured to control operation of the gears 42, 44, thus controlling the translation and the rotation.

Figure 7:
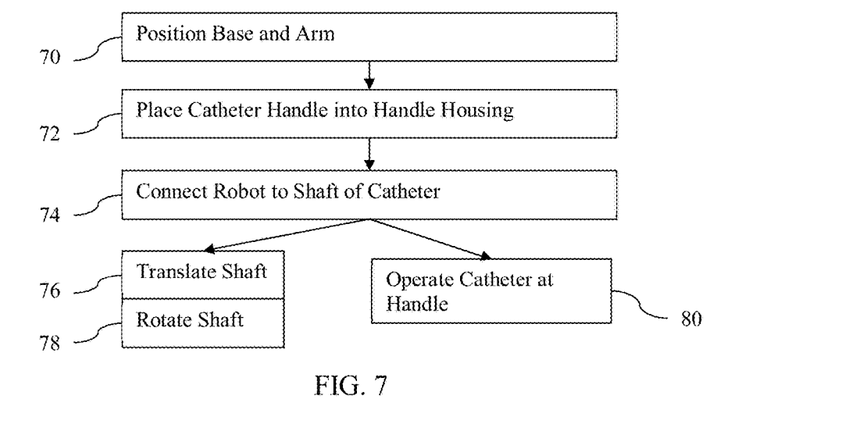
FIG. 7 is a flow chart diagram of one embodiment of a method for robotically operating a catheter.

FIG. 7 is a flow chart diagram of one embodiment of a method for robotically operating a catheter. The method includes point control of translation and/or rotation of the shaft near the access point to the patient and spaced from the handle.

The method is implemented by the system and/or robotic system of FIGS. 2 and 3 or another system. The method uses the ICE catheter and imaging system of FIG. 1 or a different catheter. The method is described below using the catheter 12 of FIG. 1 and the robotic system of FIGS. 2 and 3. Other robotic systems and/or catheters may be used.

Additional, different, or fewer acts may be provided. For example, acts 70-74 are not provided. As another example, act 80 is not provided. In yet another example, only one of act 76 or 78 is performed.

The acts are performed in the order shown or a different order. In the example of FIG. 7, acts 70-74 are performed to position for insertion or after insertion of the catheter 12 into the patient 82, and acts 76-80 are performed for use as inserted in the patient 82. Act 80 may be performed prior to or during acts 76 and/or 78. Acts 76 and 78 are performed in any order sequentially or simultaneously. Act 72 may be performed prior to act 70 and/or after act 74.

In act 70, the base 34 and arm 36 are positioned. The base 34 is positioned relative to the patient 82. Depending on the point of access of the catheter 12 to the patient, the base 34 is positioned to align the catheter 12 with the patient and point of access. FIG. 8 shows an example where the base 34 is positioned for catheter 12 insertion into the femoral artery. The base 34 is positioned on a table or bed between the legs of the patient 82. The base 34 may be positioned relative to the patient at other locations, such as for access for the radial or jugular.

The base 34 rests on the table. Alternatively, the base 34 is attached to the table, such as by suction, magnetic, or mechanically (e.g., a latch or pin system).

The arm 36 is adjusted to place the access point housing 39 at the access point and at a desired angle. A tip or exit location on the access point housing 39 is positioned against or by (e.g., within 6 inches) the already inserted sheath at the access point on the patient 82. The access point housing 39 is positioned by manual or robotic positioning of the arm 36. Upon desired positioning, the arm 36 is locked in place by one or more brakes, such as a brake activated by the knob 37.

In act 72, the handle 21 of the catheter 12 is placed in the robotic system (i.e., in the handle robot). The handle 21 is placed in the handle housing 33. The handle housing 33 is closed around the handle 21 and latched in place to hold the handle 21.

This positioning occurs while the catheter handle housing 33 connects with the base 34. In one embodiment, the catheter handle housing 33 is separable from the base 34. The handle 21 is positioned in the catheter handle housing 33 while the catheter handle housing 33 is not attached to the base.

A sterile bag may be placed around the catheter 12. One or more holes are provided in the sterile bag, such as for the catheter 12 to extend into the patient and/or for the cable from the catheter handle 21 to connect to an imaging system. In one embodiment, the entire robotic system other than power and/or control cables and catheter exit points are placed in the sterile bag. In another embodiment, holes are provided in the sterile bag for shafts for robotic control. The base 34 connects to the catheter handle housing 33 through a plastic interface with the two holes of the sterile bag. The catheter handle housing 33, the catheter 12, and the access point housing 39 are outside the sterile bag. The base 34, arm 36, and access point base 38 are in the sterile bag. Since all electronics are kept sterile by the bag, the electronics may be reused without cleaning or with a less intense cleaning. Since all parts not inside the bag are plastic or metal, these parts may be easily cleaned in-house and reused as many times as the catheter 12 is reused.

In act 74, the access point robot is connected to the shaft 20 of the catheter 12. The connection is along the shaft at a position spaced from the handle 21 of the catheter 12. The shaft 20 of the catheter 12 is connected to the access point housing 39 one or more inches away from the closest part of the handle 21.

The shaft housing 20 of the catheter 12 may be inserted into the access point housing 39, such as sliding the shaft 20 into the worm 40 with sufficient force to counter friction. Before insertion into the patient, the tip 32 of the catheter 12 is fed through an aperture of the worm 40. Alternatively, the worm 40 is a clam shell or has a removable side wall part to lay the shaft housing 20 in the access point housing 39 after insertion into the patient 82.

In one embodiment, the worm 40 and worm gears 42, 44 are positioned, after insertion of the shaft 20 into the worm 40 and/or patient 82, into the clamshell 68 as shown in FIGS. 6A and 6B. The positioning mates the gears 46, 48 with the gears 62, 64. Once positioned, the clamshell 68 is latched closed as shown in FIG. 6C. Alternatively, the worm 40 and worm gears 42, 44 are held in the access point robot during insertion of the shaft 20 into the robot.

The insertion may feed the catheter 12 into the patient, such as through an already placed sheath. The handle 21 may be placed in the catheter handle housing 33 after or during insertion of the catheter shaft 20 through the access point housing 39 and/or into the patient 82. The shaft 20 may be placed in the worm 40 after or during insertion.

In act 76, the access point robot translates the catheter 12 along a longitudinal axis of the shaft 20. Using the connection to the shaft 20 away from the handle, the shaft at the location of the connection is moved to apply push or pull force along the shaft 20. The amount of translation may be small relative to translation by moving the handle 21 for more subtle control of the catheter 12.

In one embodiment, the translation is applied by operating a worm drive. The worm 40 of the worm drive connects the robot to the shaft 20. The controller operates the motor 54 while the motor 56 is braked or not operated. The motor 56 not operating causes the tooth or teeth 70 to remain in position in the groove or grooves 52, preventing rotation of the worm 40. The motor 54 causes the shaft 60 and gear 64 to rotate. The rotation of the gear 64 rotates the worm wheel 42. The rotation of the worm wheel 42 with the threading 72 mated to the threading 50 causes the worm 40 to move forward or backward along the longitudinal axis, depending on the direction of rotation. This movement provides the translation. The worm 40 is driven along the longitudinal axis with the threaded connection to the worm wheel 42.

In act 78, the access point robot rotates the catheter 12 about a longitudinal axis of the shaft 20. Using the connection to the shaft 20 away from the handle 21, the location of the connection is moved to rotate or twist the shaft 20. The amount of rotation may be small relative to rotation by rotating the handle 21 for more subtle control of the catheter 12.

In one embodiment, the rotation is applied by operating a worm drive. The worm 40 of the worm drive connects the robot to the shaft 20. By rotating the rotational worm wheel 44 using the motor 56, the worm 40 rotates. The controller operates the motor 54 and the motor 56 simultaneously for rotation of the worm wheels 42, 44 in a same direction. The motors 54, 56 cause the shafts 58, 60 and gears 62, 64 to rotate. The rotation of the gears 62, 64 rotates the worm wheels 42, 44. The rotation of the rotation wheel 44 causes the tooth or teeth 70 to press against the sidewalls of the groove or grooves 52, causing rotation of the worm 40. The rotation of the translation wheel 42 prevents translation due to rotation of the worm 40. In other embodiments, both translation and rotation are provided simultaneously by operating the motors 54, 56 to rotate the worm wheels 42, 44 at different speeds and/or directions.

In act 80, the base or handle robot operates the catheter 12. The operation is in conjunction with translation and/or rotation by the access point robot. Alternatively, at least some movement by the access point robot of the shaft 20 is not also provided by movement of the handle 21. In either case, the translation and rotation by the access point robot is an additional operation to the movement by the handle or base robot.

In one embodiment, the controller activates a handle rotation motor. This rotates the handle 21, such as through pressure contact or other mechanical linkage. The handle 21 of the catheter 12 rotates about a longitudinal axis of the handle 21. Rotation of the knobs 29 to match rotation of the handle 21 may be provided to prevent change in steering.

In another embodiment, one or more knobs 29 are operated by the handle robot. The knobs 29 are rotated more or less than the handle 21, such as not rotating the handle and rotating one or both knobs 29. The knobs 29 are rotated to steer the catheter 12. The knobs 29 may be rotated independently of each other and the rotation of the handle 21.

During and/or after steering and/or positioning, the catheter 12 is used. For an intervention catheter, drugs may be injected from the catheter 12 or a tool on the catheter 12 is used (e.g., scissors, needle, ablation electrode, scalpel, or another instrument).

For the imaging catheter of FIG. 1, the transducer 16 is used for ultrasound scanning in a field of view 18. Ultrasound imaging is performed with the transducer. The user may view the surrounding tissue in different directions by rotating the catheter and/or other steering. Changes in bending may alter the field of view to image other anatomy or devices in the patient.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A robotic catheter system comprising:
    a threaded housing configured to hold a shaft of a catheter at a position spaced from a handle of the catheter, the threaded housing configured to hold the shaft by press or friction fit with the shaft;
    a first gear mated with the threaded housing, the first gear and the threaded housing forming a worm drive; and
    a motor configured to rotate the first gear, the threaded housing movable in response to rotation of the first gear such that the shaft of the catheter is moved.

2. The robotic catheter system of claim 1 wherein the threaded housing comprises a worm with threading on an outer surface of a cylinder, and wherein the first gear comprises a tube with threading on an inner surface and gearing on an outer surface of the tube, the threading on the inner surface mating with the threading on the outer surface of the cylinder.

3. The robotic catheter system of claim 1 wherein the threaded housing comprises a groove extending along an outer surface of a cylinder, and wherein the first gear comprises a first tube with a tooth on an inner surface, the tooth mating with the groove.

4. The robotic catheter system of claim 3 wherein the threaded housing comprises a worm with threading on the outer surface of the cylinder, and further comprising a second gear comprising a second tube with threading on an inner surface and gearing on an outer surface of the second tube, the threading on the inner surface mating with the threading on the outer surface of the cylinder.

5. The robotic catheter system of claim 1 wherein the motor is a servo motor.

6. The robotic catheter system of claim 1 wherein the first gear has teeth on an outer surface, and wherein the motor rotates the first gear by rotating a shaft with gearing mating with the teeth.

7. The robotic catheter system of claim 1 further comprising:
- a housing housing the motor;
- a base connectable with the handle of the catheter and configured for robotic manipulation of the handle; and
- an armature connecting the housing to the base.

8. The robotic catheter system of claim 7 wherein the armature is configured to hold the shaft of the catheter at a point of entry into a patient.

9. The robotic catheter system of claim 7 wherein the manipulation of the handle comprises rotation of the handle and/or steering of the catheter with steering wires.

10. The robotic catheter system of claim 1 further comprising:
- a housing housing the motor; and
- a clam shell having a hinge, the clam shell configured to accept the first gear and the threaded housing and hold the first gear and the threaded housing in place with the first gear mating with gearing connected with the motor.

11. The robotic catheter system of claim 1 wherein the worm drive, in response to operation of the motor, is configured to rotate the shaft about a longitudinal axis of the shaft.

12. The robotic catheter system of claim 1 wherein the worm drive, in response to operation of the motor, is configured to translate the shaft along a longitudinal axis of the shaft.

13. A robotic catheter system comprising:
- a threaded housing configured to hold a shaft of a catheter at a position spaced from a handle of the catheter, wherein the threaded housing comprises a groove extending along an outer surface of a cylinder and a worm with threading on the outer surface of the cylinder;
- a first gear mated with the threaded housing, the first gear and the threaded housing forming a worm drive, wherein the first gear comprises a first tube with a tooth on an inner surface, the tooth mating with the groove;
- a second gear comprising a second tube with threading on an inner surface and gearing on an outer surface of the second tube, the threading on the inner surface mating with the threading on the outer surface of the cylinder; and
- a motor configured to rotate the first gear, the threaded housing movable in response to rotation of the first gear such that the shaft of the catheter is moved.

14. The robotic catheter system of claim 13 wherein the motor is a servo motor.

15. The robotic catheter system of claim 13 wherein the first gear has teeth on an outer surface, and wherein the motor rotates the first gear by rotating a shaft with gearing mating with the teeth.

16. The robotic catheter system of claim 13 further comprising:
- a housing housing the motor;
- a base connectable with the handle of the catheter and configured for robotic manipulation of the handle; and
- an armature connecting the housing to the base.

17. The robotic catheter system of claim 16 wherein the armature is configured to hold the shaft of the catheter at a point of entry into a patient.

18. The robotic catheter system of claim 16 wherein the manipulation of the handle comprises rotation of the handle and/or steering of the catheter with steering wires.

19. The robotic catheter system of claim 13 further comprising:
- a housing housing the motor; and
- a clam shell having a hinge, the clam shell configured to accept the first gear and the threaded housing and hold the first gear and the threaded housing in place with the first gear mating with gearing connected with the motor.

* * * * *